(12) United States Patent
Hiraide et al.

(10) Patent No.: US 10,631,784 B2
(45) Date of Patent: Apr. 28, 2020

(54) PORTABLE ELECTRONIC APPARATUS

(71) Applicant: SEIKO EPSON CORPORATION, Tokyo (JP)

(72) Inventors: Takuya Hiraide, Okaya (JP); Hironori Hasei, Azumino (JP); Noriaki Hiraide, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 16/029,099

(22) Filed: Jul. 6, 2018

(65) Prior Publication Data

US 2019/0021662 A1 Jan. 24, 2019

(30) Foreign Application Priority Data

Jul. 19, 2017 (JP) ................. 2017-139731

(51) Int. Cl.
| | |
|---|---|
| *H05K 7/00* | (2006.01) |
| *A61B 5/00* | (2006.01) |
| *A61B 5/024* | (2006.01) |
| *A61B 5/11* | (2006.01) |
| *H02S 10/40* | (2014.01) |
| *G04G 21/02* | (2010.01) |
| *H02S 40/38* | (2014.01) |
| *A61B 5/0205* | (2006.01) |
| *H02S 20/30* | (2014.01) |
| *G04R 20/02* | (2013.01) |
| *G04C 10/02* | (2006.01) |
| *G04G 19/00* | (2006.01) |
| *G04G 9/00* | (2006.01) |

(52) U.S. Cl.
CPC ............ *A61B 5/681* (2013.01); *A61B 5/0022* (2013.01); *A61B 5/0205* (2013.01); *A61B 5/02427* (2013.01); *A61B 5/02438* (2013.01); *A61B 5/1112* (2013.01); *A61B 5/1126* (2013.01); *A61B 5/742* (2013.01); *G04C 10/02* (2013.01); *G04G 21/025* (2013.01); *G04R 20/02* (2013.01); *H02S 10/40* (2014.12); *H02S 20/30* (2014.12); *H02S 40/38* (2014.12); *A61B 2560/0214* (2013.01); *G04G 9/007* (2013.01); *G04G 19/00* (2013.01)

(58) Field of Classification Search
CPC .................................. H05K 5/00; H05K 7/00
See application file for complete search history.

(56) References Cited

U.S. PATENT DOCUMENTS

| | | | |
|---|---|---|---|
| 4,165,604 A * | 8/1979 | Matsumura | G04C 10/02 368/288 |
| 2002/0028988 A1 | 3/2002 | Suzuki et al. | |
| 2014/0268522 A1* | 9/2014 | Tanaka | A61B 5/681 361/679.01 |

FOREIGN PATENT DOCUMENTS

JP 2006-320735 A 11/2006

* cited by examiner

*Primary Examiner* — Jerry Wu
(74) *Attorney, Agent, or Firm* — Oliff PLC

(57) ABSTRACT

A wrist apparatus includes a case, a solar battery that is provided in the case, and an optical sensor unit as a biological information measurement unit that is provided in the case, measures biological information, and is disposed at a position overlapping the solar battery in a plan view of a light reception surface of the solar battery.

8 Claims, 8 Drawing Sheets

PORTABLE ELECTRONIC APPARATUS

CROSS-REFERENCES TO RELATED APPLICATIONS

This application claims priority to Japanese Patent Application No. 2017-139731, filed Jul. 19, 2017, the entirety of which is herein incorporated by reference.

BACKGROUND

1. Technical Field

The present invention relates to a portable electronic apparatus.

2. Related Art

In the related art, there is a portable electronic apparatus which is mounted on the wrist of a wearer (user) with a band or the like, measures biological information such as a pulse wave of the wearer, and has a clock display function. For example, JP-A-2006-320735 discloses a wearable life support apparatus which is mounted on the body of a wearer, and acquires biological information or body motion information by using a mounted optical pulse wave sensor or acceleration sensor. In the wearable life support apparatus, since electric energy for operating various sensors increases, a method for reducing power consumption is proposed through power source management, for example, message display to a user is turned off during sleeping, or a specific sensor is stopped during sleeping.

However, in power source management in the wearable life support apparatus which is an example of a portable electronic apparatus, in a case where a sensor with high power consumption or various sensors are mounted, electric energy of a power source may be insufficient, and thus a user may experience inconvenience such as not being able to perform measurement or the need for a charging operation. Meanwhile, in order to secure power supply, measures such as installing a solar battery capable of obtaining a sufficient power generation amount (charge amount) are conceivable. However, there is concern that a sufficient plane area of the solar battery may not be secured, and a sufficient power generation amount may not be obtained, depending on a disposition position of the solar battery.

SUMMARY

An advantage of some aspects of the invention is to solve at least a part of the problems described above, and the invention can be implemented as the following forms or application examples.

Application Example 1

A portable electronic apparatus according to this application example includes a case; a solar battery that is provided in the case; and a biological information measurement unit that is provided in the case, measures biological information, and is disposed at a position overlapping the solar battery in a plan view from a normal direction to a light reception surface of the solar battery.

According to the portable electronic apparatus according to the application example, since the solar battery and the biological information measurement unit are disposed to overlap each other in the plan view, a plane area of the solar battery can be increased such that a power generation amount can be increased, and thus a charge amount of a power source can be increased. Consequently, it is possible to reduce concern that electric energy of the power source may be insufficient.

Application Example 2

In the portable electronic apparatus according to the application example, it is preferable that the solar battery is annular in the plan view, and wherein the centroid of the solar battery overlaps the biological information measurement unit in the plan view.

According to this application example, a balance of the portable electronic apparatus can be improved, and thus mountability for a user can be improved.

Application Example 3

It is preferable that the portable electronic apparatus according to the application example further includes a display unit that is provided in the case; and a secondary battery that is provided in the case, and is electrically connected to the solar battery, the solar battery overlaps the display unit, and the display unit is disposed between the solar battery and the secondary battery.

According to this application example, a user can easily visually recognize display on the display unit without being blocked by the secondary battery.

Application Example 4

In the portable electronic apparatus according to the application example, it is preferable that the secondary battery is disposed between the display unit and the biological information measurement unit.

According to this application example, it is possible to block so-called stray light which is light incident toward the solar battery for power generation but enters the inside of the case as leakage light through a gap or the like from the solar battery side, with the secondary battery, and can thus to reduce the influence of external light on the biological information measurement unit.

Application Example 5

In the portable electronic apparatus according to the application example, it is preferable that the portable electronic apparatus has a region in which the solar battery, the display unit, and the biological information measurement unit overlap each other in the plan view.

According to this application example, it is possible to increase a plane area of the solar battery and thus to increase a power generation amount.

Application Example 6

In the portable electronic apparatus according to the application example, it is preferable that the biological information measurement unit includes a measurement window portion provided in the case, and the measurement window portion is disposed at a position overlapping the solar battery in the plan view.

According to this application example, it is possible to increase a plane area of the solar battery and thus to increase a power generation amount.

Application Example 7

It is preferable that the portable electronic apparatus according to the application example further includes a circuit board that is provided in the case, and a distance between the circuit board and the solar battery is shorter than a distance between the circuit board and the biological information measurement unit in a sectional view from a direction which is orthogonal to a normal direction to the light reception surface.

According to this application example, since the distance between the circuit board and the solar battery is short, a transmission loss of power generated by the solar battery can be reduced, and thus it is possible to increase charging efficiency.

Application Example 8

It is preferable that the portable electronic apparatus according to the application example further includes a circuit board that is provided in the case, and a distance between the circuit board and the solar battery is longer than a distance between the circuit board and the biological information measurement unit in a sectional view from a direction which is orthogonal to a normal direction to the light reception surface.

Since the distance between the circuit board and the solar battery is made long, the solar battery is hardly influenced by heat generation from the circuit board or other constituent elements. Consequently, it is possible to suppress a temperature increase in the solar battery and thus to increase power generation efficiency in the solar battery.

Application Example 9

In the portable electronic apparatus according to the application example, it is preferable that the circuit board has a first surface and a second surface which is different from the first surface, and the solar battery is connected to the first surface, and the biological information measurement unit is connected to the second surface.

According to this application example, routing of a wiring for connection can be made the minimum, and it is also possible to block so-called stray light which is light incident toward the solar battery for power generation but enters the inside of the case as leakage light through a gap or the like from the solar battery side, with the circuit board, and can thus to reduce the influence of external light on the biological information measurement unit.

Application Example 10

It is preferable that the portable electronic apparatus according to the application example further includes an illumination unit that illuminates the display unit, the illumination unit is connected to the first surface of the circuit board, and the biological information measurement unit is connected to the second surface of the circuit board.

According to this application example, routing of a wiring for connection can be made the minimum, and it is also possible to block light emitted from the illumination unit with the circuit board, and can thus to reduce the influence of stray light on the biological information measurement unit.

Application Example 11

In the portable electronic apparatus according to the application example, it is preferable that the biological information measurement unit includes a light emitting portion and a light receiving portion, and the light emitting portion is disposed outside the light receiving portion in the plan view.

According to this application example, since the light receiving portion is located inside the light emitting portion, it is possible to suppress external light from entering the light receiving portion and thus to reduce the influence of the external light on the biological information measurement unit.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
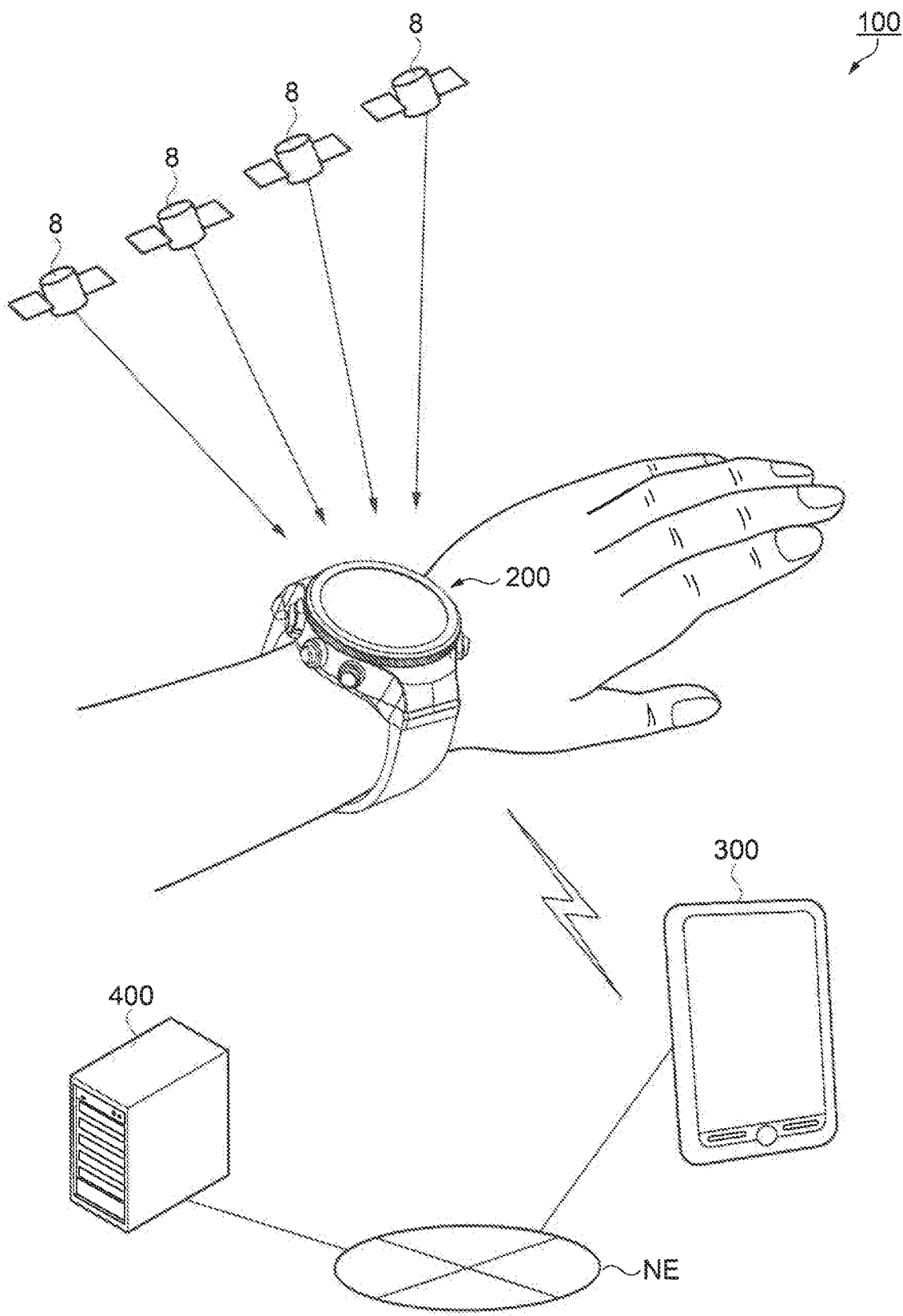
FIG. 1 is a schematic configuration diagram illustrating a summary of a workout support system to which a wrist apparatus as a portable electronic apparatus is applied.

Hereinafter, embodiments of a system related to the invention will be described. The embodiments described below are not intended to improperly limit the content of the invention disclosed in the appended claims. All constituent elements described in each embodiment are not essential constituent elements of the invention.

1. Method of Present Embodiment

First, a description will be made of a workout support system as an example of a system to which a portable electronic apparatus according to the present embodiment of the invention is applied. Hereinafter, as an example of a portable electronic apparatus, a description will be made of a wrist apparatus (wearable apparatus) which is mounted on the wrist of a user and includes a pulse wave sensor or a body motion sensor.

A wrist apparatus as a portable electronic apparatus used for a workout support system is provided with a solar battery on a display unit side, and includes a pulse wave sensor acquiring pulse wave information as biological information of a user or a body motion sensor acquiring action information of the user. The wrist apparatus includes a global positioning system (GPS) acquiring position information of the user as an example of a positioning system using a position information satellite called a global navigation satellite system (GNSS). A portable electronic apparatus is not limited to the wrist apparatus, and may be a wearable apparatus which is mounted on other parts of the user, such as the neck or the ankle.

The pulse wave sensor as an example of a biological information measurement unit acquires pulse wave information such as a pulse rate. As the pulse wave sensor, for example, a photoelectric sensor (optical sensor) is used. In this case, the photoelectric sensor may detect reflected light or transmitted light of light applied to a living body. Since an amount of applied light absorbed or reflected in the living body differs depending on a blood flow rate in a blood vessel, sensor information detected by the photoelectric sensor is converted into a signal corresponding to the blood flow rate, and information regarding pulsation can be acquired by analyzing the signal. However, a pulse wave sensor is not limited to a photoelectric sensor, and may employ other sensors such as an electrocardiograph or an ultrasonic sensor.

The photoelectric sensor (optical sensor) is required to receive necessary light and to block unnecessary light. For example, in a case of a pulse wave sensor, reflected light including a pulse wave component reflected at a subject (particularly, a part including a measurement target blood vessel) which is a measurement target object is required to be received, and other light is a noise component and is thus required to be blocked.

The body motion sensor is a sensor detecting motion of the user. As the body motion sensor, an acceleration sensor, an angular velocity sensor, an azimuth sensor (geomagnetic sensor), a pressure sensor (altitude sensor), or the like may be used, but other sensors may be used.

The GPS stands for a global positioning system, and is a satellite positioning system for measuring the current position on the earth on the basis of a plurality of satellite signals. The GPS has a function of acquiring position information of a user by performing positioning calculation by using GPS time information and orbit information, and a time correction function in a clock function.

2. Workout Support System

Next, with reference to FIG. 1, a description will be made of a configuration of a workout support system to which a wrist apparatus as a portable electronic apparatus is applied. FIG. 1 is a schematic configuration diagram illustrating a summary of a workout support system to which a wrist apparatus as a portable electronic apparatus is applied.

A workout support system 100 according to the present embodiment includes, as illustrated in FIG. 1, a wrist apparatus 200 as a portable electronic apparatus which is a detection apparatus including a pulse wave sensor as a biological sensor (photoelectric sensor) or a GPS; a portable apparatus 300 as a workout support apparatus; and a server 400 as an information processing apparatus which is connected to the portable apparatus 300 via a network NE.

The GPS as a global navigation satellite system provided in the wrist apparatus 200 has a function of receiving electric waves (satellite signals) from GPS satellites 8, and correcting internal time or acquiring position information by positioning calculation. Each of the GPS satellites 8 is an example of a position information satellite which orbits on a predetermined orbit in the sky above the earth and transmits high-frequency electric waves superimposed with a navigation message to the ground. In the following description, an electric wave superimposed with a navigation message will be referred to as a satellite signal.

A satellite signal from the GPS satellite 8 includes GPS time information which is considerably accurate, and a time correction parameter for correcting a time error. The wrist apparatus 200 may receive a satellite signal (electric wave) from a single GPS satellite 8 so as to acquire time information by using the GPS time information and the time correction parameter included therein.

The satellite signal also includes orbit information indicating a position on an orbit of the GPS satellite 8. The wrist apparatus 200 may perform positioning calculation by using the GPS time information and the orbit information. The positioning calculation is performed on the premise that some extent of an error is included in an internal time of the wrist apparatus 200. In other words, a time error is also an unknown number in addition to x, y and z parameters for specifying a three-dimensional position of the wrist apparatus 200. Thus, the wrist apparatus 200 may receive satellite signals (electric waves) transmitted from, for example, three or more GPS satellites 8, and may perform positioning calculation by using GPS time information and orbit information included therein so as to acquire position information of the current location.

The portable apparatus 300 as a workout support apparatus may be formed of, for example, a smart phone or a tablet terminal apparatus. The portable apparatus 300 is connected to the wrist apparatus 200 in which a pulse wave sensor as a biological sensor which is a photoelectric sensor via short-range radio communication such as Bluetooth (registered trademark) communication or wired communication (not illustrated). The portable apparatus 300 receives measurement information from the wrist apparatus 200, and notifies a user of processed pulse wave information or body motion information of the user, or position information. However, the portable apparatus 300 may be variously modified, for example, by including an optical sensor unit 40, a body motion sensor unit 170, or a GPS reception unit 160 which will be described later included in the wrist apparatus 200.

The wrist apparatus 200 and the portable apparatus 300 have a Bluetooth function, and the portable apparatus 300 and the wrist apparatus 200 are connected to each other via Bluetooth communication, for example, Bluetooth Low Energy (also called Bluetooth 4.0). Bluetooth Low Energy focuses on power saving, and can considerably save power compared with an old version so as to increase available time of the wrist apparatus.

The portable apparatus 300 may be connected to the server 400 such as a personal computer (PC) or a server system via the network NE. The network NE here may employ various networks NE such as a wide area network (WAN), a local area network (LAN), a mobile phone communication network, and short-range radio communication. In this case, the server 400 is realized as a processing storage unit which receives pulse wave information or body motion information measured by the wrist apparatus 200 or data processed by the portable apparatus 300 from the portable apparatus 300 via the network NE, and stores the information or the data.

In the embodiment, the wrist apparatus 200 is not required to be directly connected to the network NE as long as the wrist apparatus 200 can perform communication with the portable apparatus 300. Therefore, a configuration of the wrist apparatus 200 can be simplified. However, in the workout support system 100, a modification may occur in which the portable apparatus 300 is omitted, and the wrist apparatus 200 is directly connected to the server 400. In this case, the wrist apparatus 200 has a function, which is a function of the portable apparatus 300, of processing measurement information, and a function of transmitting measurement information to the server 400 or receiving information from the server 400.

The workout support system 100 is not limited to a configuration including the server 400. For example, processes or functions performed in the workout support system 100 may be realized by the portable apparatus 300. For example, the portable apparatus 300 such as a smart phone has restrictions in processing capability, a storage region, and a battery capacity compared with a server system, but may secure sufficient processing capability and the like in consideration of the recent capability improvement. Therefore, if the needs for the processing capability and the like are satisfied, the portable apparatus 300 can independently realize processes or functions performed in the workout support system 100 according to the present embodiment.

The workout support system 100 according to the present embodiment is not limited to being realized by three apparatuses. For example, the workout support system 100 may include two or more apparatuses among the wrist apparatus 200, the portable apparatus 300, and the server 400. In this case, processes performed in the workout support system 100 may be performed by any one of apparatuses, and may be distributed to and performed by a plurality of apparatuses. The workout support system 100 according to the present embodiment may include apparatuses which are different from the wrist apparatus 200, the portable apparatus 300, and the server 400. However, in a case of taking into consideration improvement of terminal capability or a use form, there may be an embodiment in which the workout support system 100 according to the present embodiment is realized by the wrist apparatus 200.

The workout support system 100 of the present embodiment includes a memory storing information (for example, programs or pieces of data), and a processor which operates on the basis of the information stored in the memory. In the processor, for example, a function of each unit may be realized by individual hardware, and may be realized by integrated hardware. The processor may be, for example, a central processing unit (CPU). However, the processor is not limited to a CPU, and may employ various processors such as a graphics processing unit (GPU) or a digital signal processor (DSP). The processor may be a hardware circuit using an ASIC. The memory may be, for example, a semiconductor memory such as a static random access memory (SRAM) or a dynamic random access memory (DRAM), may be a register, may be a magnetic storage device such as a hard disk device, and may be an optical storage device such as an optical disc device. For example, the memory stores computer readable commands, and the commands are executed by the processor such that a function of each unit of the workout support system 100 is realized. The commands here may be commands forming a program, and may be commands for instructing a hardware circuit to perform an operation.

3. Wrist Apparatus

Figure 2:
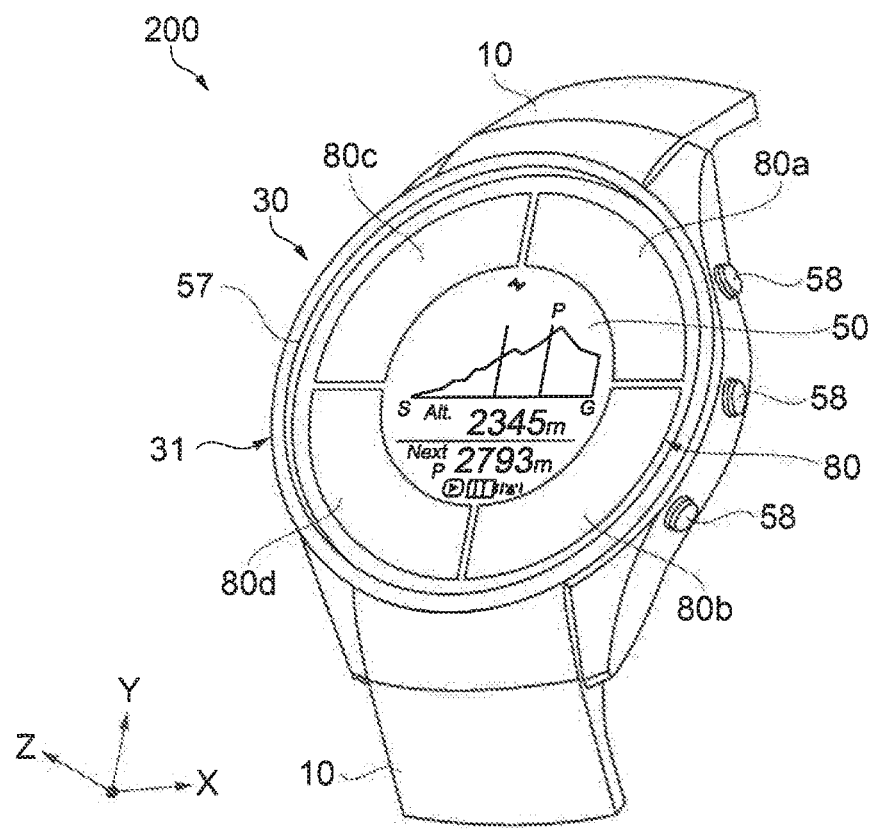
FIG. 2 is an exterior perspective view from a front side (display surface side) illustrating a schematic configuration of the wrist apparatus.
Figure 3:
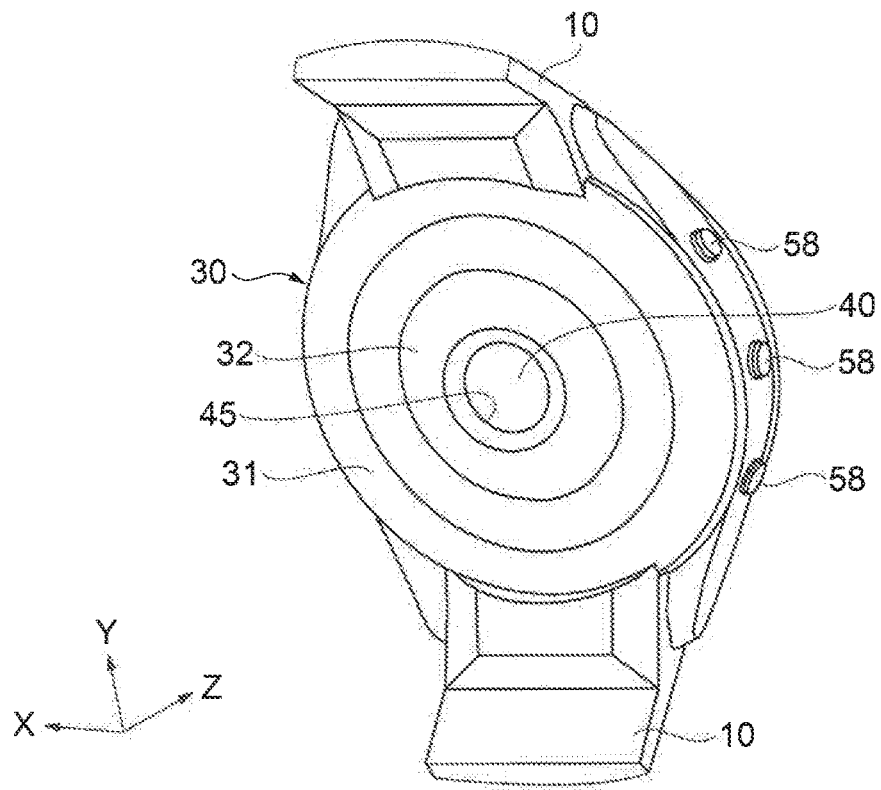
FIG. 3 is an exterior perspective view from a rear side illustrating a schematic configuration of the wrist apparatus.
Figure 4:
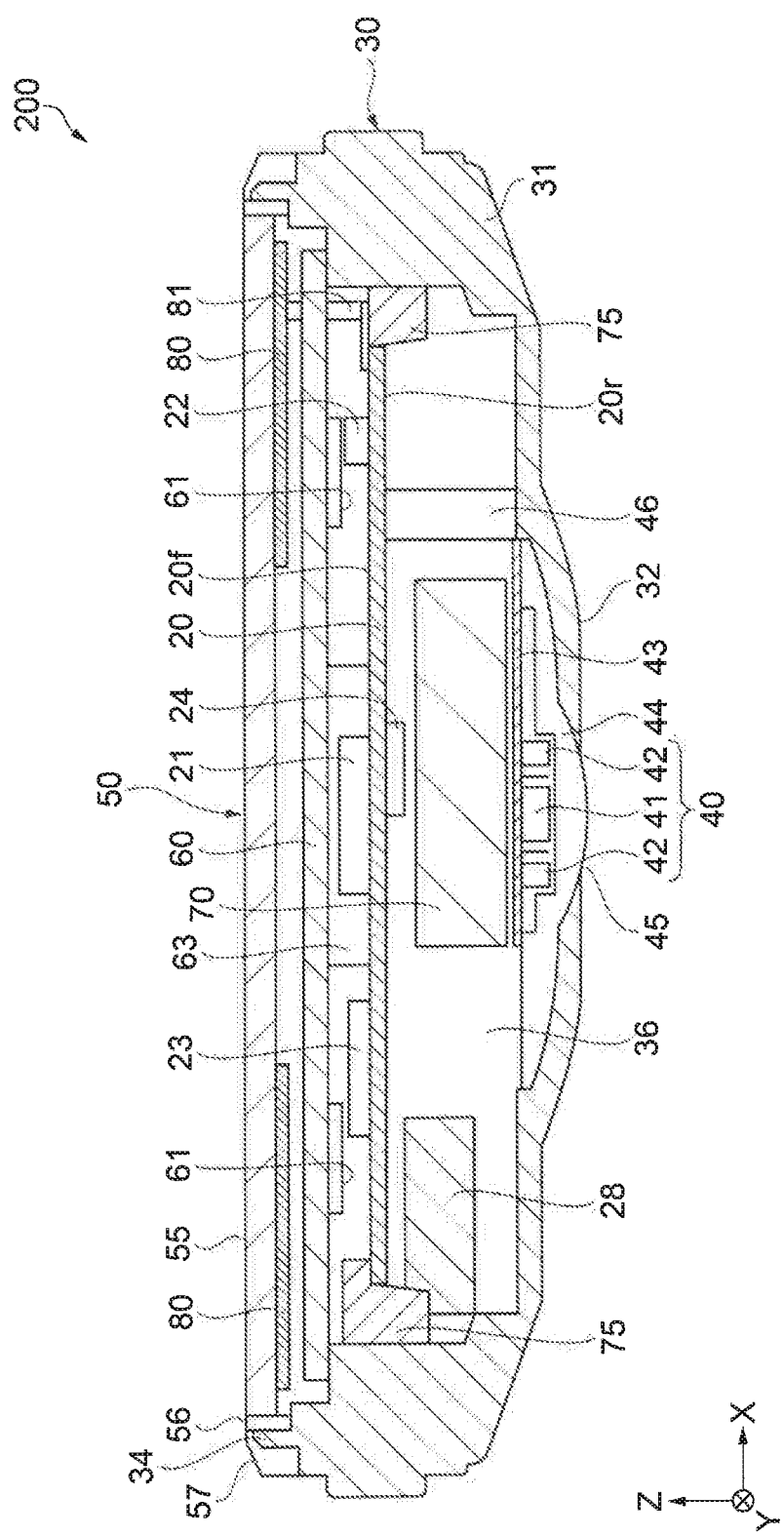
FIG. 4 is a sectional view illustrating a configuration of the wrist apparatus.
Figure 5:
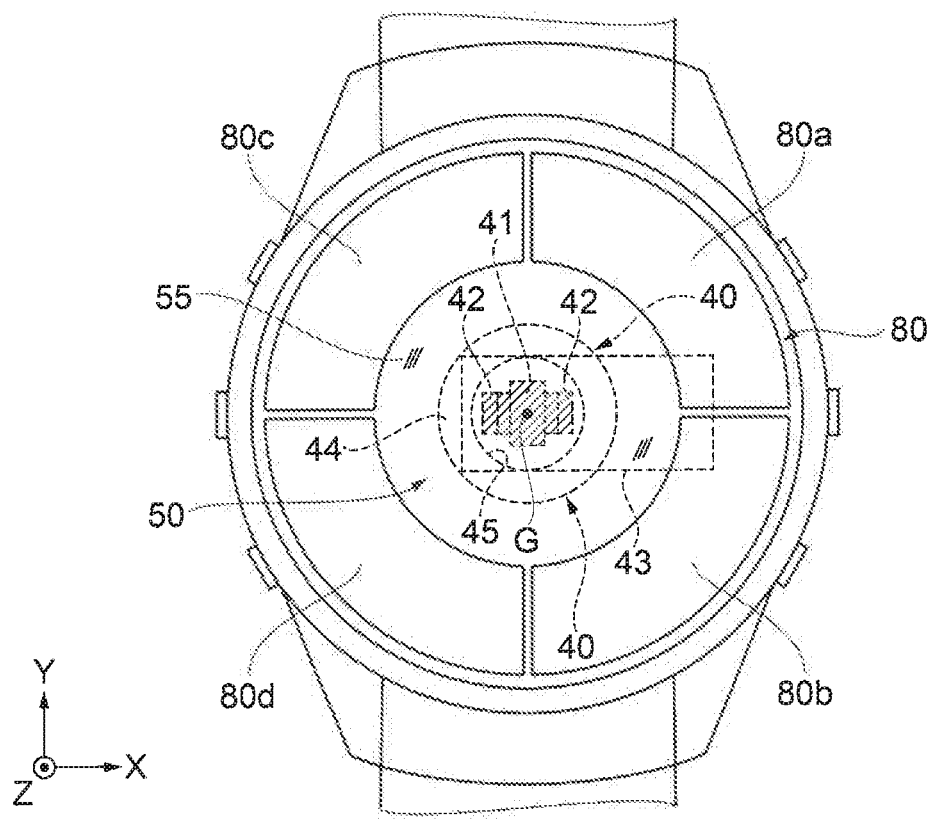
FIG. 5 is a plan view illustrating a configuration of the wrist apparatus.
Figure 6:
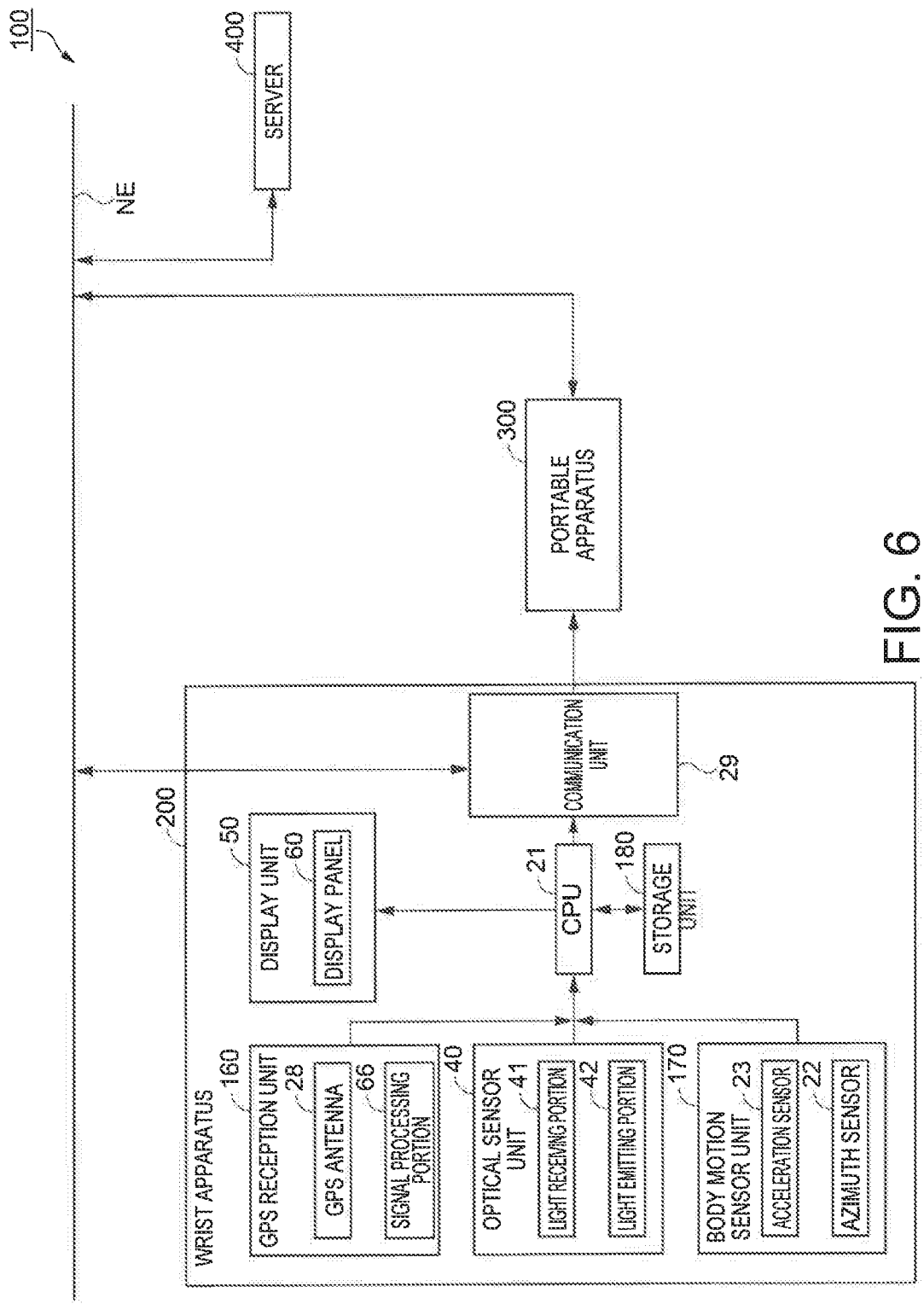
FIG. 6 is a functional block diagram illustrating a schematic configuration of the wrist apparatus.
Figure 7:
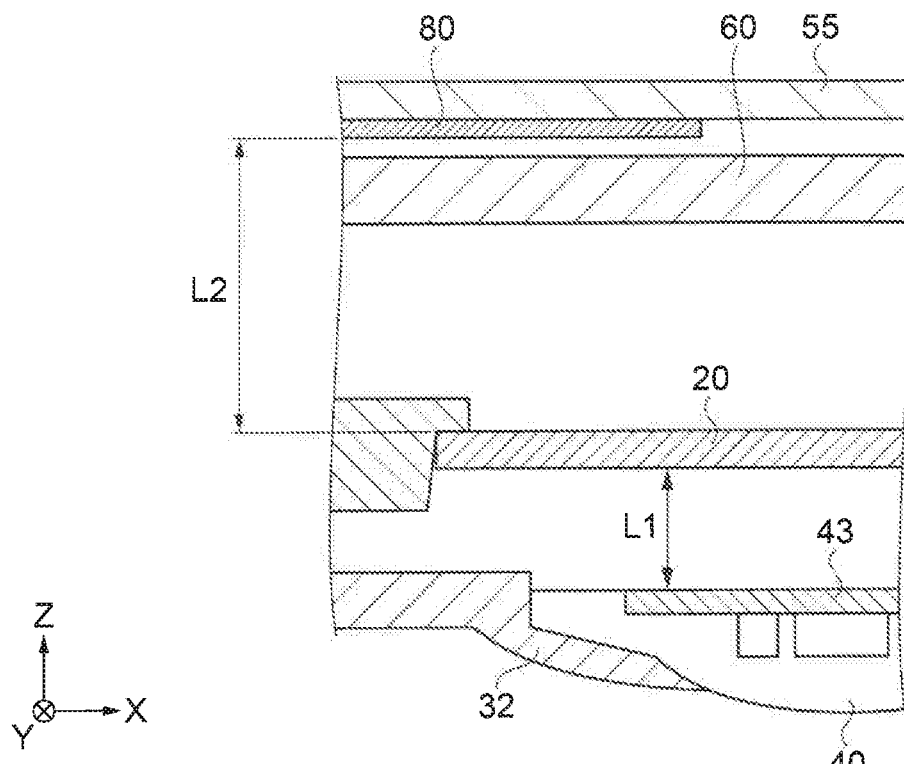
FIG. 7 is a partial sectional view illustrating a disposition example 1 of constituent elements of the wrist apparatus.
Figure 8:
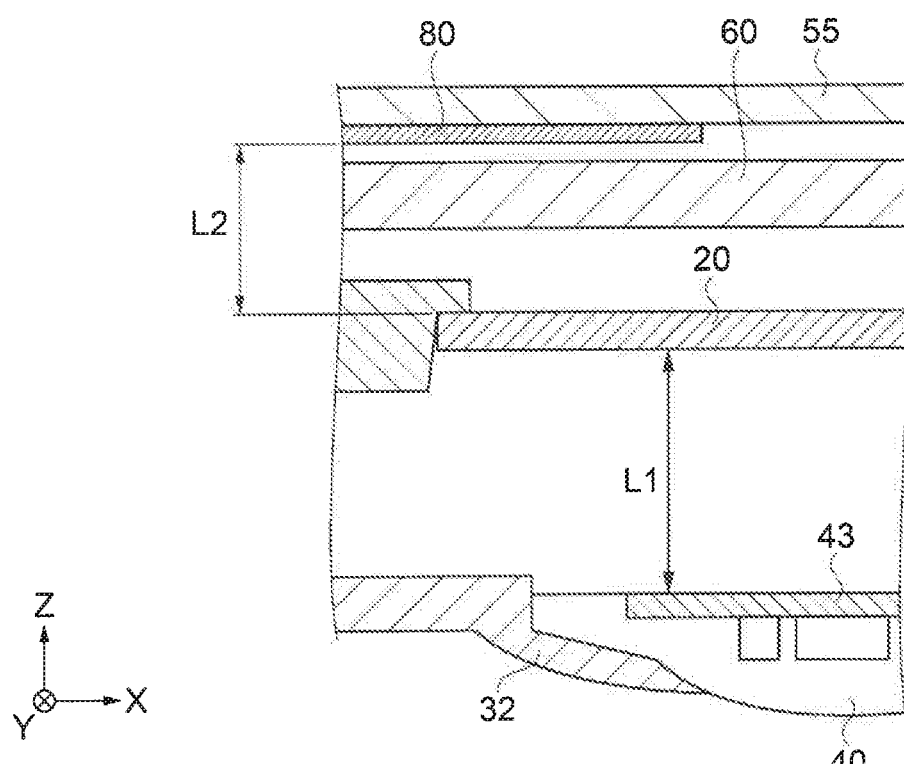
FIG. 8 is a partial sectional view illustrating a disposition example 2 of constituent elements of the wrist apparatus.

Next, with reference to FIGS. 2 to 8, a description will be made of a configuration of the wrist apparatus as a portable electronic apparatus. FIG. 2 is an exterior perspective view from a front side (display surface side) illustrating a schematic configuration of the wrist apparatus. FIG. 3 is an exterior perspective view from a rear side illustrating a schematic configuration of the wrist apparatus. FIG. 4 is a sectional view illustrating a configuration of the wrist apparatus. FIG. 5 is a plan view illustrating a configuration of the wrist apparatus. FIG. 6 is a functional block diagram illustrating a schematic configuration of the wrist apparatus. FIG. 7 is a partial sectional view illustrating a disposition example 1 of constituent elements of the wrist apparatus. FIG. 8 is a partial sectional view illustrating a disposition example 2 of constituent elements of the wrist apparatus.

In the following description of the wrist apparatus 200, when an apparatus main body 30 is worn by a user, a side located on a target object side which is a target part for measuring biological information or the like will be referred to as "a rear side or a rear surface side", and a display surface side of the apparatus main body 30 opposite side thereto will be referred to as "a front side or a front surface side". A measurement "target object (target part)" will be referred to as a "subject" in some cases. A coordinate system is set with a case 31 of the wrist apparatus 200 as a reference, and a direction which becomes distant from the case 31 in a normal direction to light reception surfaces 80a, 80b, 80c, and 80d of a panel forming a solar battery 80 is defined as a positive Z axis direction (+Z axis direction). Two axes orthogonal to the Z axis are defined as XY axes, and, particularly, a direction in which band portions 10 are attached to the case 31 is set to the Y axis. The light reception surfaces 80a, 80b, 80c, and 80d are surfaces via which light is incident to the solar battery 80.

FIG. 2 is a perspective view in which the wrist apparatus 200 to which the band portion 10 is fixed is viewed from the +Z axis direction which is a direction directed toward the front side (display unit 50 side) from the rear side corresponding to a subject side in a mounting state. FIG. 3 is a perspective view in which the wrist apparatus 200 is viewed from the rear side opposite to FIG. 2, that is, from the −Z axis direction. FIG. 4 is a sectional view in which the wrist apparatus 200 is viewed from the +Y axis direction.

As illustrated in FIGS. 2 to 4, the wrist apparatus 200 as a portable electronic apparatus is mounted on a predetermined part (for example, a measurement target part such as the wrist) of the user, and measures pulse wave information, position information, or the like. The wrist apparatus 200 includes the apparatus main body 30 which includes the case 31 and is in close contact with the user so as to measure pulse wave information or the like, and a pair of band portions 10 which is attached to the apparatus main body 30 and is used to mount the apparatus main body 30 on the user.

The apparatus main body 30 including the case 31 is provided with the display unit 50, the annular solar battery 80 including the light reception surfaces 80a, 80b, 80c, and 80d of the panel directed in the +Z axis direction and disposed at an outer edge part of the display unit 50, and a measurement window portion 45 corresponding to the optical sensor unit 40 (refer to FIG. 4) as a biological information measurement unit. The display unit 50 and a part of the solar battery 80 may be disposed to overlap each other in a plan view from the +Z axis direction (the normal direction to the light reception surfaces 80a, 80b, 80c, and 80d). A plurality of operation units (operation buttons) 58 are provided on an outer surface of the apparatus main body 30, and a bezel 57 is provided to annularly surround an outer edge of the display unit 50. However, the wrist apparatus 200 is not limited to such a configuration, and may be variously modified by omitting some of the constituent elements or adding other constituent elements thereto.

The apparatus main body 30 has the case 31 which is open on the front side. The measurement window portion 45 of the optical sensor unit 40 is provided at the top of a protrusion portion 32 protruding from the rear surface which is a rear side surface of the case 31 on the rear side of the case 31. The optical sensor unit 40 as a biological information measurement unit is disposed at a position corresponding to the measurement window portion 45 in a plan view from the +Z axis direction, and a transparent cover 44 is inserted into the measurement window portion 45. The transparent cover 44 may protrude from the top of the protrusion portion 32. At least a part of the measurement window portion 45 is preferably disposed at a position overlapping the solar battery 80 in a plan view from the +Z axis direction. As mentioned above, since at least a part of the measurement window portion 45 of the optical sensor unit 40 is disposed at the position overlapping the solar battery 80 annularly provided, a plane area of the solar battery 80, that is, a light reception area can be increased, and thus it is possible to increase an amount of generated power.

The case 31 may be formed by using, for example, metal such as stainless steel, or a resin. A configuration of the case 31 is not limited to an integrated configuration, and may be a configuration of being divided into a plurality of parts, for example, the case 31 may have a dual structure in which a lid is provided on the side mounted on a user.

The apparatus main body 30 is provided with the bezel 57 on an outer circumferential side of a projection 34 which projects and stands in the +Z axis direction at the outer edge of the opening of the case 31 located on the front side of the apparatus main body 30, and is also provided with a windshield plate 55 (a glass plate in this example) which is a transparent plate as a top plate for protecting the internal structure inside the bezel 57. The windshield plate 55 is disposed to close the opening of the case 31 in a plan view from a direction facing the light reception surfaces 80a, 80b, 80c, and 80d of the solar battery 80, that is, from the +Z axis direction. The windshield plate 55 is attached on an inner edge side of the projection 34 of the case 31 via a joint member 56 such as a packing or an adhesive. An internal space 36 which is a closed space is provided inside the case 31 surrounded by the case 31 and the windshield plate 55 closing the opening of the case 31.

The windshield plate 55 is not limited to a glass plate, and may be a member which is a light-transmissive member through which the display unit 50 can be viewed and is made of materials such as transparent plastic other than glass as long as the materials have the strength sufficient to protect element components accommodated in the internal space 36, for example, a liquid crystal display (LCD 60) forming the display unit 50.

As illustrated in FIG. 4, as element components forming the wrist apparatus 200, for example, a circuit board 20, an azimuth sensor 22 and an acceleration sensor 23 as sensors included in the body motion sensor unit 170 (refer to FIG. 6), a GPS antenna 28, the optical sensor unit 40, the liquid crystal display (hereinafter, referred to as the display panel 60) forming the display unit 50, an illumination unit 61 of the display panel 60, a secondary battery 70 (lithium secondary battery), and the solar battery 80 are stored in the internal space 36 of the case 31. However, the apparatus main body 30 is not limited to the configuration illustrated in FIG. 4, and may be added with other sensors such as a pressure sensor for calculating an elevation or a temperature sensor for measuring a temperature, or a vibrator. The circuit board 20 is connected to connection wires with the above-described element components, a central processing unit (CPU) 21 which is a control circuit controlling the respective sensors forming the wrist apparatus 200 or the display unit 50 or a control circuit including a drive circuit, and other circuit elements 24.

Among the element components forming the wrist apparatus 200 disposed in the internal space 36, the circuit board 20, the optical sensor unit 40, the secondary battery 70, the display panel 60, and the solar battery 80 are disposed in an order of the solar battery 80, the display panel 60, the circuit board 20, the secondary battery 70, and the optical sensor unit 40 from the windshield plate 55 side. The solar battery 80 is disposed to cover at least a part of the display unit 50.

As mentioned above, the display panel 60 forming the display unit 50 is disposed between the solar battery 80 and the secondary battery 70 due to the disposition of the element components in the case 31. With this disposition, the user can easily visually recognize display on the display unit 50 without being blocked by the secondary battery 70.

Since the display panel 60 forming the display unit 50 is disposed between the solar battery 80 and the optical sensor unit 40 in the case 31, it is possible to block so-called stray light which is light incident toward the solar battery 80 for power generation but enters the inside of the case 31 as leakage light through a gap or the like from the solar battery 80 side, with the display panel 60, and can thus to reduce the influence of external light (stray light) on the optical sensor unit 40.

The secondary battery 70 is disposed between the display unit 50 and the optical sensor unit 40 due to the disposition of the element components in the case 31. With this disposition, it is possible to block so-called stray light which is light incident toward the solar battery 80 for power generation but enters the inside of the case 31 as leakage light through a gap or the like from the solar battery 80 side, with the secondary battery 70, and can thus to reduce the influence of external light on the optical sensor unit 40.

Preferably, there is provided a region in which the solar battery 80, the display panel 60 forming the display unit 50, and the optical sensor unit 40 overlap each other in a plan view from the +Z axis direction. With this overlapping disposition, it is possible to increase a plane area of the solar battery 80 and thus to increase a power generation amount.

As illustrated in FIG. 7, preferably, the circuit board 20, the optical sensor unit 40, and the solar battery 80 are disposed such that a distance L2 (the shortest distance between the circuit board 20 and the solar battery 80) between the circuit board 20 and the solar battery 80 is longer than a distance L1 (the shortest distance between the circuit board 20 and the optical sensor unit 40) between the circuit board 20 and the optical sensor unit 40 in a sectional view from the −Y axis direction which is orthogonal to the +Z axis direction (the normal direction to the light reception surfaces 80a, 80b, 80c, and 80d). As mentioned above, if the distance L2 between the circuit board 20 and the solar battery 80 is made long, the solar battery 80 is hardly influenced by heat generation from the circuit board 20 or other constituent elements. In other words, it is possible to suppress a temperature increase in the solar battery 80 and thus to suppress a reduction in power generation efficiency in the solar battery 80.

As illustrated in FIG. 8, the circuit board 20, the optical sensor unit 40, and the solar battery 80 are disposed such that the distance L2 (the shortest distance between the circuit board 20 and the solar battery 80) between the circuit board 20 and the solar battery 80 may be shorter than the distance L1 (the shortest distance between the circuit board 20 and the optical sensor unit 40) between the circuit board 20 and the optical sensor unit 40 in a sectional view from the −Y axis direction which is orthogonal to the +Z axis direction (the normal direction to the light reception surfaces 80*a*, 80*b*, 80*c*, and 80*d*). As mentioned above, if the distance L2 between the circuit board 20 and the solar battery 80 is made short, a transmission loss of power generated by the solar battery 80 can be reduced, and thus it is possible to increase charging efficiency.

Since the circuit board 20 is disposed between the solar battery 80 and the optical sensor unit 40 in the case 31, it is possible to block so-called stray light which is light incident toward the solar battery 80 for power generation but enters the inside of the case 31 as leakage light through a gap or the like from the solar battery 80 side, with the circuit board 20, and can thus to reduce the influence of external light (stray light) on the optical sensor unit 40.

Hereinafter, each element component will be described also with reference to the functional block diagram of FIG. 6.

The circuit board 20 has a front surface 20*f* as a first surface and a rear surface 20*r* as a second surface which is different from the front surface 20*f* and is an opposite surface to the front surface 20*f*, and ends thereof are attached to the inside of the case 31 via a circuit case 75. The azimuth sensor 22 and the acceleration sensor 23 as sensors included in the body motion sensor unit 170, the CPU 21 as a control circuit, and the like are mounted on the front surface 20*f* of the circuit board 20, and other circuit elements 24 and the like are mounted on the rear surface 20*r*.

The display panel 60 and the solar battery 80 are connected to the front surface 20*f* of the circuit board 20 via a connection wiring portion 63 and a connection wiring portion 81 formed of flexible boards or the like. The optical sensor unit 40 is electrically connected to the rear surface 20*r* of the circuit board 20 which is an opposite surface to the front surface 20*f* via a connection wiring portion 46 formed of a flexible board or the like. With such disposition, routing of a wiring for connection can be made the minimum, and it is also possible to block stray light which is light incident for power generation but enters the inside of the case as leakage light from the solar battery 80 side, with the circuit board 20, and can thus to reduce the influence of external light on the optical sensor unit 40. The circuit case 75 can guide the secondary battery 70 or the like.

The azimuth sensor (geomagnetic sensor) 22 or the acceleration sensor 23 included in the body motion sensor unit 170 may measure information related to motion of the user's body, that is, body motion information. The azimuth sensor (geomagnetic sensor) 22 or the acceleration sensor 23 outputs a body motion detection signal which is a signal changing depending on body motion of the user, and transmits the body motion detection signal to the CPU 21 as a control circuit.

The CPU 21 forms a control circuit or the like controlling a circuit which controls the GPS reception unit 160 including the GPS antenna 28, a circuit which drives the optical sensor unit 40 so as to measure a pulse wave, a circuit which drives the display unit 50 (display panel 60), a circuit which drives the body motion sensor unit 170 so as to measure body motion information, and a power generation circuit in the solar battery 80. The CPU 21 transmits pulse wave information or body motion information measured at each part, or position information of the user to a communication unit 29 as necessary.

The GPS antenna 28 is included in the GPS reception unit 160 along with a signal processing portion 66, and receives a plurality of satellite signals. The signal processing portion 66 performs positioning calculation on the basis of the plurality of satellite signals received by the GPS antenna 28, and acquires as position information of the user.

The communication unit 29 transmits the pulse wave information or the body motion information, or the position information of the user transmitted from the CPU 21 to the portable apparatus 300 or the like as necessary.

The optical sensor unit 40 as a biological information measurement unit measures a pulse wave or the like, and includes the light receiving portion 41, and a plurality of (in the present embodiment, two) light emitting portions 42 disposed on both sides of the light receiving portion 41, that is, outside the light receiving portion 41 (on the outer circumferential side of the case 31) in a plan view. In other words, the light receiving portion 41 is disposed further toward the center of the case 31 than the light emitting portion 42 in a plan view from the +Z axis direction. Therefore, in a plan view from the +Z axis direction, a distance from the outer edge of the case 31 to the optical sensor unit 40 increases, and thus light emitted from the light emitting portions 42, and natural light or illumination light (hereinafter, referred to as external light) which is different from light emitted from the light emitting portions 42 and reflected from the user hardly reach the light receiving portion 41, so that the influence of the external light on the light receiving portion 41 can be reduced. The number of light emitting portions 42 is not limited to two, and may be one or three or more. The light receiving portion 41 and the two light emitting portions 42 are attached to one surface of a sensor substrate 43, and is covered with a transparent cover 44 which is formed of a light-transmissive member made of a thermosetting resin. A portion of the transparent cover 44 including a region corresponding to the light receiving portion 41 and the two light emitting portions 42 is inserted into the measurement window portion 45 provided in the case 31. The transparent cover 44 may protrude from the top of the protrusion portion 32 of the case 31.

As described above, in the optical sensor unit 40, a subject (measurement target object) is irradiated with light emitted from the light emitting portion 42, and the reflected light is received by the light receiving portion 41, and thus pulse wave information is measured. The optical sensor unit 40 outputs a signal detected by the pulse wave sensor including the light emitting portion 42 and the light receiving portion 41, as a pulse wave measurement signal. For example, a photoelectric sensor is used as the optical sensor unit 40. In this case, there may be a method in which reflected light or transmitted light of light applied to a living body (the wrist of the user) from the light emitting portion 42 is detected by the light receiving portion 41. In this method, since an amount of applied light absorbed or reflected in the living body differs depending on a blood flow rate in a blood vessel, sensor information detected by the photoelectric sensor is converted into a signal corresponding to the blood flow rate, and information regarding pulsation can be acquired by analyzing the signal. However, a pulse wave sensor is not limited to a photoelectric sensor, and may employ other sensors such as an electrocardiograph or an ultrasonic sensor.

As illustrated in FIG. 5, at least a part of the optical sensor unit 40 is disposed to overlap the solar battery 80 to overlap the annularly formed solar battery 80 in a plan view from the direction (+Z axis direction) facing the light reception surfaces 80*a*, 80*b*, 80*c*, and 80*d* of the solar battery 80. Here, the optical sensor unit 40 includes a region up to the outer edge of the transparent cover 44 or a region up to the outer edge of the sensor substrate 43 in a plan view from the +Z axis direction. In the present embodiment, the sensor substrate 43 overlaps the solar battery 80 annularly formed. The term "overlapping" indicates a state of S>0 if an area where the solar battery 80 and the optical sensor unit 40 overlap each other in a plan view from the +Z axis direction is indicated by S.

As mentioned above, since at least a part of the optical sensor unit 40 is disposed at a position overlapping the annularly disposed solar battery 80 in a plan view from the +Z axis direction, a plane area of the solar battery 80 can be increased such that a power generation amount can be increased, and thus a charge amount of the power source can be increased.

As illustrated in FIG. 5, at least a part of the annularly formed optical sensor unit 40 is preferably disposed to overlap the centroid G of the solar battery 80 in a plan view from the +Z axis direction. With the disposition of the optical sensor unit 40 and the solar battery 80, biasing of the centroid in the apparatus main body 30 can be suppressed. In other words, the centroid G of the solar battery 80 and the optical sensor unit 40 are located at the center of the apparatus main body 30 in a plan view from the +Z axis direction. Therefore, since the centroid of the apparatus main body 30 is located at the center of the apparatus main body 30 in a plan view from the +Z axis direction, a balance (centroid position) is favorable, and thus mountability for a user can be improved. The centroid G may be replaced with the center of mass. In a case of a solid object, the centroid G may be defined in a structure of the solid object, or may be defined in a space. The term "overlapping the centroid" may be defined as a state of overlapping the centroid in a case where the position of the centroid is projected onto a two-dimensional plane or a predetermined target object when viewed from a predetermined direction.

The display unit 50 can be visually recognized by the user through the windshield plate 55, and is formed of numbers or icons displayed on a display member such as the display panel 60, or time display indicators. In other words, in the present embodiment, various pieces of information such as measured biological information or information indicating a workout state are displayed by using the display panel 60, and the display is presented to the user from the front side (in the +Z axis direction). As the display member, instead of the display panel 60 which is a liquid crystal display, an organic electroluminescence (EL) display, an electrophoretic display (EPD), or a light emitting diode (LED) display may be used.

The illumination unit 61 functions as a backlight of the display panel 60. The illumination unit 61 is connected to the front surface 20f as a first surface of the circuit board 20. Since the illumination unit 61 is connected to the circuit board 20 as described above, routing of a wiring for connection can be made the minimum, and it is also possible to block light emitted from the illumination unit 61 with the circuit board 20, and can thus to reduce the influence of stray light on the optical sensor unit 40.

The secondary battery 70 has both of polarity terminals connected to the circuit board 20 via a connection board (not illustrated), and supplies power to a circuit controlling a power source. The power is converted into predetermined voltages by the circuit, so as to be supplied to respective circuits, and thus to drive a circuit which drives the optical sensor unit 40 to measure a pulse, a circuit which drives the display panel 60, and a control circuit (CPU 21) which controls the respective circuits. The secondary battery 70 is charged via a pair of charging terminals which are electrically connected to the circuit board 20 via a conduction member (not illustrated) such as a coil spring, or is charged by using power generated by the solar battery 80.

The solar battery (solar cell) 80 generates power by converting light energy of external light such as sunlight into power by using a photoelectromotive force effect. The solar battery 80 of the present embodiment is disposed to be divided into four panels between the windshield plate 55 and the display panel 60, and the light reception surfaces 80a, 80b, 80c, and 80d of the respective panels are disposed to be directed in the +Z axis direction. The solar battery 80 is disposed on the outer edge side of the display panel 60 (the outer edge of the display unit 50), and is formed in a so-called annular shape (ring shape) of which the central portion has a penetration hole. In other words, the solar battery 80 has an outer circumference along the outer edge of the case 31 and an inner circumference of which a circumferential length is shorter than that of the outer circumference. In this configuration, the annular solar battery 80 using the four panels is exemplified, but the solar battery 80 may be formed of an integrated panel. In a case where the solar battery 80 is formed of a plurality of panels, any number of panels may be used. Any shapes of panels forming the solar battery 80 may be used.

A storage unit 180 stores biological information such as a pulse wave from the optical sensor unit 40, position information from the GPS reception unit 160, and body motion information from the body motion sensor unit 170, under the control of the CPU 21.

According to the wrist apparatus 200 as a portable electronic apparatus, since at least a part of the optical sensor unit 40 is disposed at the position overlapping the annularly disposed solar battery 80 in a plan view from the +Z axis direction, a plane area of the solar battery 80 can be increased such that a power generation amount can be increased, and thus a charge amount of the power source can be increased. Consequently, it is possible to reduce inconvenience such as not being able to perform measurement or the need for a charging operation due to insufficiency of electric energy of the power source (secondary battery 70). The centroid G of the solar battery 80 and the optical sensor unit 40 are located at the center of the apparatus main body 30 in a plan view from the +Z axis direction. Therefore, since the centroid of the apparatus main body 30 is located at the center of the apparatus main body 30 in a plan view from the +Z axis direction, a balance (centroid position) is favorable, and thus mountability for a user can be improved.

3.1 Modification Example of Disposition of Solar Battery and Optical Sensor

Figure 9:
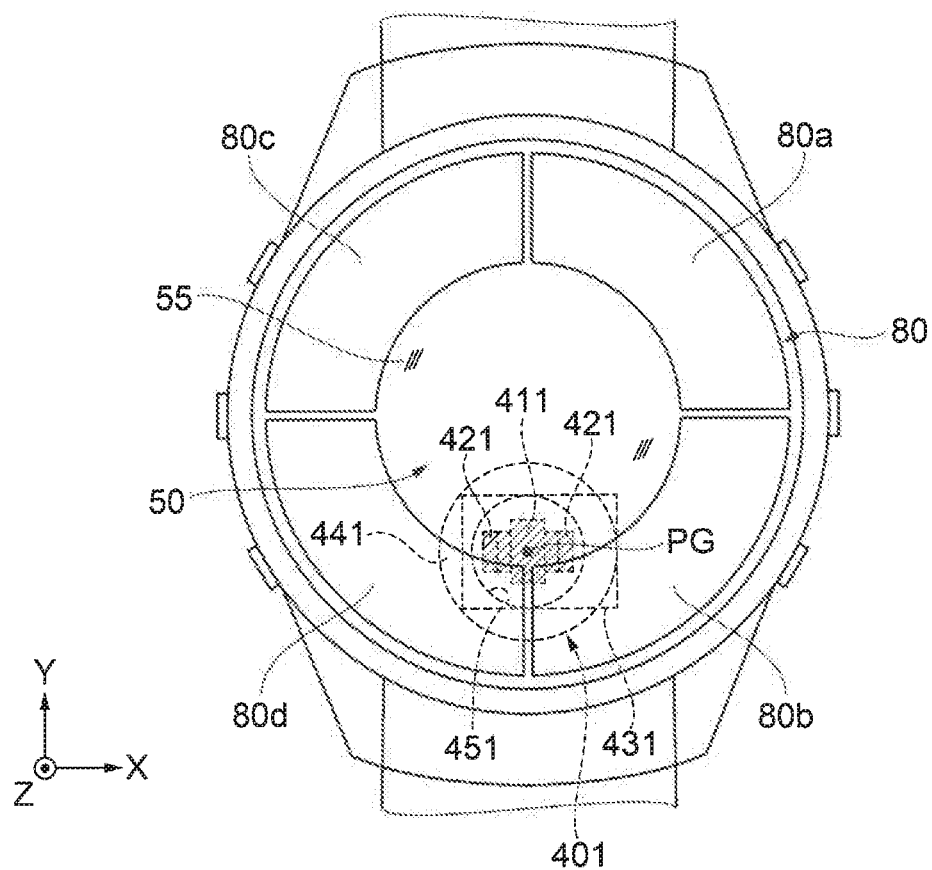
FIG. 9 is a plan view illustrating Modification Example 1 of disposition of a solar battery and an optical sensor.
Figure 10:
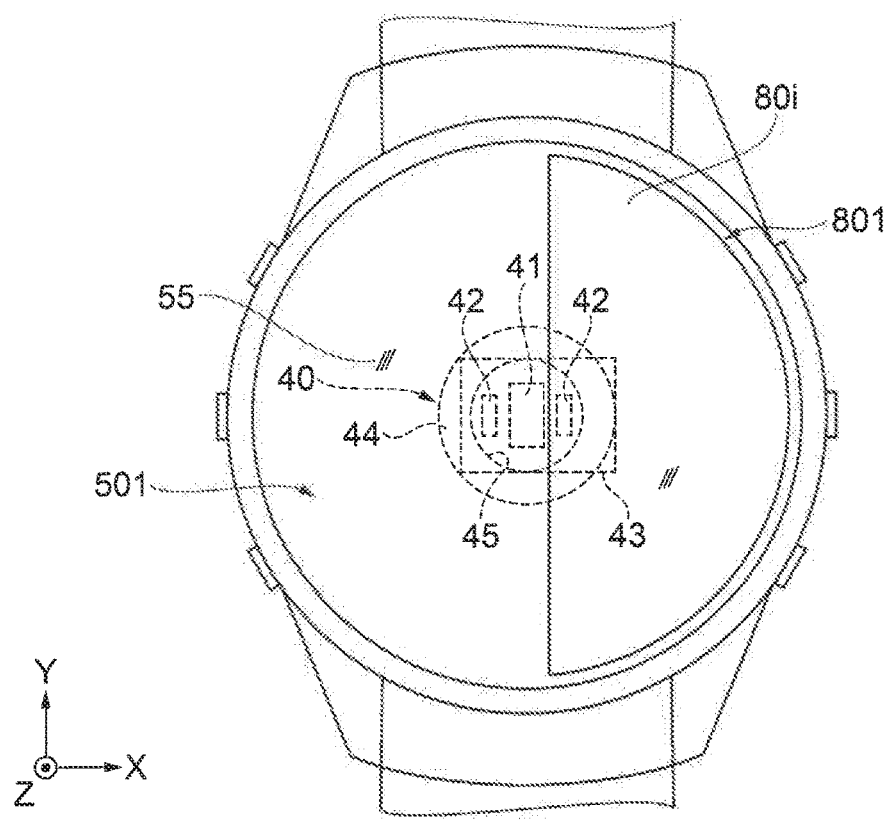
FIG. 10 is a plan view illustrating Modification Example 2 of disposition of a solar battery and an optical sensor.
Figure 11:
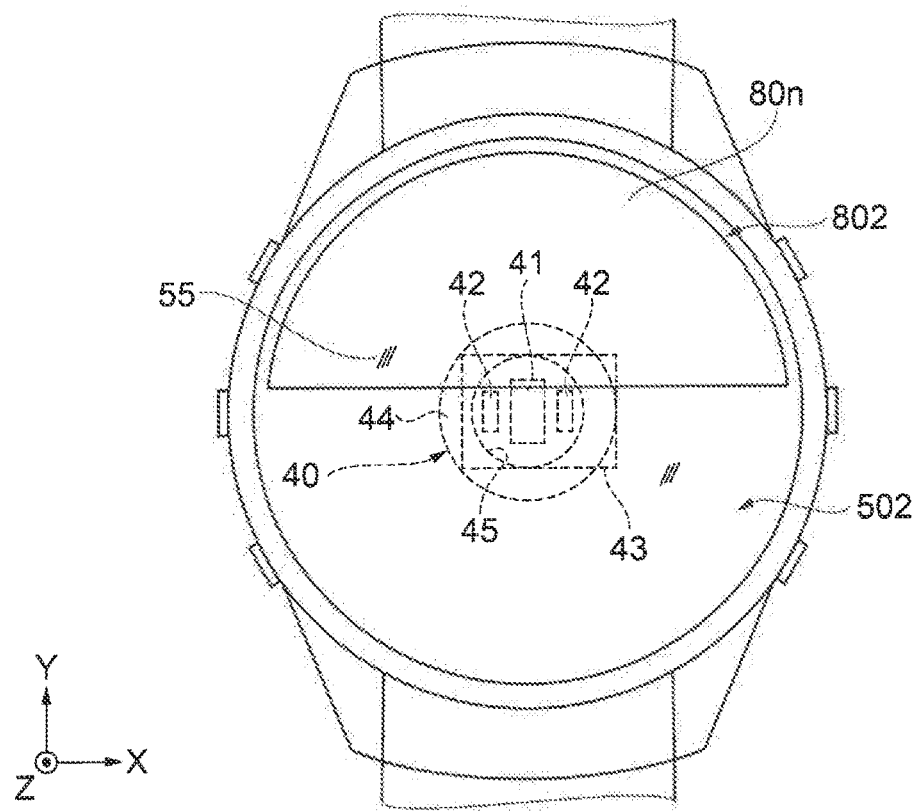
FIG. 11 is a plan view illustrating Modification Example 3 of disposition of a solar battery and an optical sensor.

In the above description, a description has been made of the configuration in which the annular solar battery 80 is disposed on the outer edge side of the display panel 60, and the optical sensor unit 40 is disposed on the central portion side of the solar battery 80 in a plan view from the +Z axis direction, but a disposition configuration of the solar battery 80 and the optical sensor unit 40 is not limited thereto. A disposition and a configuration (shape) of the solar battery 80 and a disposition of the optical sensor unit 40 may be realized as described in the following modification examples, for example. A disposition configuration of the solar battery 80 and the optical sensor unit 40 is not limited to the modification examples, and may employ other configurations. Hereinafter, with reference to FIGS. 9 to 11, Modification Example 1 to Modification Example 3 of disposition of the solar battery and the optical sensor will be described in this order. FIGS. 9 to 11 are plan views illustrating modification examples of disposition of the solar battery and optical sensor, in which FIG. 9 illustrates Modification Example 1, FIG. 10 illustrates Modification Example 2, and FIG. 11 illustrates Modification Example 3.

Modification Example 1

With reference to FIG. 9, a description will be made of Modification Example 1 of disposition of the solar battery and the optical sensor. As illustrated in FIG. 9, in the same manner as in the above-described embodiment, a solar battery 80 according to Modification Example 1 is located on the outer edge side of the display panel 60 (refer to FIG. 4) between the windshield plate 55 and the display panel 60, and light reception surfaces 80a, 80b, 80c, and 80d of four respective panels which are disposed to be separate from each other are disposed to be directed in the +Z axis direction. The solar battery 80 is formed in an annular shape (ring shape) of which the central portion has a penetration hole, and the display unit 50 is provided at the central portion. The solar battery 80 may be formed of an integrated panel not divided.

Here, an optical sensor unit 401 includes a sensor substrate 431 connected to light emitting portions 421 and a light receiving portion 411, a transparent cover 441 covering the above-described constituent elements, and a measurement window portion 451 into which a part of the transparent cover 441 is inserted. The optical sensor unit 401 is disposed at a position where the centroid PG of the optical sensor unit 401 is deviated in the −Y axis direction in a plan view from the +Z axis direction. Consequently, at least a part of the optical sensor unit 401, for example, a substantially half of the optical sensor unit 401 in the −Y axis direction overlaps the solar battery 80 in a plan view from the +Z axis direction in this configuration.

According to the disposition of Modification Example 1, since at least a part of the optical sensor unit 401 is disposed at the position overlapping the annularly disposed solar battery 80 in a plan view from the +Z axis direction, a plane area of the solar battery 80 can be increased such that a power generation amount can be increased, and thus a charge amount of the power source can be increased.

Modification Example 2

With reference to FIG. 10, a description will be made of Modification Example 2 of disposition of the solar battery and the optical sensor. As illustrated in FIG. 10, a solar battery 801 according to Modification Example 2 is formed of a semicircular single panel of which an outer circumferential side forms a circular arc-shaped outer edge and a center side forms a substantially linear outer edge along the Y axis between the windshield plate 55 and the display panel 60 (refer to FIG. 4). The solar battery 801 is disposed on the +X axis side (three o'clock side) of the case 31. Therefore, a display unit 501 is disposed on the −X axis side (nine o'clock side) of the case 31. A light reception surface 80i of the panel forming the solar battery 801 is disposed to be directed in the +Z axis direction.

Here, the optical sensor unit 40 includes at least the sensor substrate 43 connected to the light emitting portions 42 and the light receiving portion 41, and is located at the center of the case 31 in a plan view from the +Z axis direction. In other words, the optical sensor unit 40 is disposed to partially overlap the substantially linear outer edge side of the solar battery 801 along the Y axis in a plan view from the +Z axis direction. A configuration of the optical sensor unit 40 is the same as described above, and thus a description thereof will be omitted here.

According to the disposition of Modification Example 2, since at least apart of the optical sensor unit 40 is disposed at a position overlapping the solar battery 801 disposed in a semicircular shape in a plan view from the +Z axis direction, a plane area of the solar battery 801 can be increased such that a power generation amount can be increased, and thus a charge amount of the power source can be increased.

The +X axis side (three o'clock side) of the case 31 is often located at the fingertip side of the user when the wrist apparatus 200 is mounted on the user's wrist, and is thus hardly hooked by clothes (sleeve) of the user. Therefore, in a case where the solar battery 801 is disposed on the +X axis side (three o'clock side) of the case 31 as in Modification Example 2, it is possible to increase a probability that sunlight may be received and also to perform more efficient power generation.

Modification Example 3

With reference to FIG. 11, a description will be made of Modification Example 3 of disposition of the solar battery and the optical sensor. As illustrated in FIG. 11, a solar battery 802 according to Modification Example 3 is formed of a semicircular single panel of which an outer circumferential side forms a circular arc-shaped outer edge and a center side forms a substantially linear outer edge along the X axis between the windshield plate 55 and the display panel 60 (refer to FIG. 4). The solar battery 802 is disposed on the +Y axis side (twelve o'clock side) of the case 31. Therefore, a display unit 502 is disposed on the −Y axis side (six o'clock side) of the case 31. A light reception surface 80n of the panel forming the solar battery 802 is disposed to be directed in the +Z axis direction.

Here, the optical sensor unit 40 includes at least the sensor substrate 43 connected to the light emitting portions 42 and the light receiving portion 41, and is located at the center of the case 31 in a plan view from the +Z axis direction. In other words, the optical sensor unit 40 is disposed to partially overlap the substantially linear outer edge side of the solar battery 802 along the X axis. A configuration of the optical sensor unit 40 is the same as described above, and thus a description thereof will be omitted here.

According to the disposition of Modification Example 3, since at least apart of the optical sensor unit 40 is disposed at a position overlapping the solar battery 802 disposed in a semicircular shape in a plan view from the +Z axis direction, a plane area of the solar battery 802 can be increased such that a power generation amount can be increased, and thus a charge amount of the power source can be increased.

In the embodiment, as an example of a positioning system using a position information satellite, a description has been made of the GPS using the GPS satellite 8 as a position information satellite included in a global navigation satellite system (GNSS), but this is only an example. The global navigation satellite system may include other systems such as Galileo (EU), GLONASS (Russia), or BeiDou (China), or a positioning information satellite transmitting a satellite signal, for example, a stationary satellite or a quasi-zenith satellite such as SBAS. In other words, the wrist apparatus 200 may be configured to acquire any one of date information, time information, position information, and speed information obtained by processing electric waves (radio signals) from position information satellites including satellites other than the GPS satellites 8. Instead of the global navigation satellite system, a regional navigation satellite system (RNSS) may be used.

What is claimed is:

1. A portable electronic apparatus comprising:
a case;
a solar battery that is provided in the case and annular in a plan view from a normal direction to a lioght reception surface of the solar battery;
a biological information measurement unit that is provided in the case, measures biological information, and is disposed at a position overlapping the solar battery in the plan view;
a display panel that is disposed between the solar battery and a secondary battery; and
a circuit board that is provided in the case,
wherein a distance between the circuit board and the solar battery is shorter than a distance between the circuit board and the biological information measurement unit in a sectional view from a direction which is orthogonal to the normal direction to the light reception surface, the solar battery is disposed on an outer edge side of the display panel, and a centroid of the solar battery overlaps the biological information measurement unit in the plan view.

2. The portable electronic apparatus according to claim 1, wherein the display panel is provided in the case, and the secondary battery is provided in the case and electrically connected to the solar battery.

3. The portable electronic apparatus according to claim 2, wherein the secondary battery is disposed between the display panel and the biological information measurement unit.

4. The portable electronic apparatus according to claim 2, wherein the portable electronic apparatus has a region in which the solar battery, the display panel, and the biological information measurement unit overlap each other in the plan view.

5. The portable electronic apparatus according to claim 1, wherein the biological information measurement unit includes a measurement window portion provided in the case, and
the measurement window portion is disposed at a position overlapping the solar battery in the plan view.

6. The portable electronic apparatus according to claim 1, wherein the circuit board has a first surface and a second surface which is different from the first surface, and
the solar battery is connected to the first surface, and the biological information measurement unit is connected to the second surface.

7. The portable electronic apparatus according to claim 6, further comprising:
an illumination unit that illuminates the display panel,
wherein the illumination unit is connected to the first surface of the circuit board.

8. The portable electronic apparatus according to claim 1, wherein the biological information measurement unit includes a light emitting portion and a light receiving portion, and
the light emitting portion is disposed outside the light receiving portion in the plan view.

* * * * *